United States Patent [19]

Harris

[11] Patent Number: 4,548,607
[45] Date of Patent: Oct. 22, 1985

[54] IMPLANTABLE MANUALLY ACTUATED MEDICATION DISPENSING SYSTEM

[75] Inventor: Donald L. Harris, Miami Beach, Fla.

[73] Assignee: Cordis Corporation, Miami, Fla.

[21] Appl. No.: 484,572

[22] Filed: Apr. 13, 1983

[51] Int. Cl.⁴ .............................................. A61M 1/00
[52] U.S. Cl. ..................................... 604/891; 604/153
[58] Field of Search ............... 604/151, 152, 153, 891, 604/141, 185; 137/256; 222/255

[56] References Cited

U.S. PATENT DOCUMENTS

| | | | |
|---|---|---|---|
| 3,492,996 | 2/1970 | Fountain | 604/185 |
| 3,768,508 | 10/1973 | Schulte | 604/9 |
| 4,013,074 | 3/1977 | Siposs | 604/891 |
| 4,221,219 | 9/1980 | Tucker | 604/141 |

*Primary Examiner*—C. Fred Rosenbaum
*Assistant Examiner*—Karen Kaechele
*Attorney, Agent, or Firm*—Lockwood, Alex, Fitzgibbon & Cummings

[57] ABSTRACT

An implantable manually-actuated dispensing system includes a housing wherein a reservoir and dispensing port are provided. Medicament within the reservoir is urged through the dispensing port in predetermined uniform dosages by a fluid circuit which serially includes a safety pump and a metering pump. The safety pump is first actuated and released to cause a quantity of medicament to be advanced through the fluid circuit into the chamber of the metering pump. The metering pump is next actuated to cause a predetermined dosage from the advanced medicament to be dispensed through the dispensing port. Check valves prevent reverse flow through the circuit and prevent medicament from entering the metering pump except upon actuation and release of the safety pump.

17 Claims, 7 Drawing Figures

IMPLANTABLE MANUALLY ACTUATED MEDICATION DISPENSING SYSTEM

BACKGROUND OF THE INVENTION

The present invention is directed generally to dispensing systems, and more particularly to an implantable manually-actuated micro-infusion pump system for dispensing prescribed dosages of a fluid medicament within the human body.

Implanted manually-actuated micro-infusion pump systems are advantageously employed when specific dosages of a medicament are to be administered within the human body at various times over an extended time period, as in the treatment of diabetes, cancer, pain, and many other diseases.

Typically, in the treatment of diabetes a dispensing system comprising a combined pump and medicament reservoir system is subcutaneously implanted in soft tissue close to the delivery site, such as over the peritoneum and abdominal muscles, and a catheter is utilized to deliver insulin to the site. Alternatively, the reservoir is implanted remotely from the site and connected to a pump system by means of a flexible catheter. When insulin is required actuation of the pump system is accomplished by the patient applying pressure on the skin surface overlying the pump.

For effective treatment it is generally required that the medicament is dispensed in measured dosages. Consequently, it is necessary that a known volume of medicament be dispensed with each actuation of the pump system, so that the user can determine the total dosage dispensed by the number of pump actuations. In the case of insulin treatment of diabetes, for example, the pump system may administer 0.1 milliliters of insulin with each actuation, so that a typical post-meal dosage of 0.6 milliliters, for example, may be administered by six (6) successive actuations of the pump system.

One drawback of previous implantable manually-actuated micro-infusion pump systems has been their susceptibility to externally applied pressures, causing them to inadvertently dispense doses, or to dispense inaccurate doses, or to permit uncontrolled flow of medicament into the body. Moreover, such pump systems must be sealed against body fluids, must hold a sufficient quantity of medicament so as to avoid the need for frequent refills, and must be refillable to preclude interruption of the medicament schedule. Furthermore, such pump systems must be physically small so as to be readily implantable without unnecessary disturbance to the body.

The present invention is directed to a manually-actuated micro-infusion pump system which satisfies these requirements, and is convenient to operate and economical to manufacture.

Accordingly, it is a general object of the present invention to provide a new and improved manually-actuated implantable microinfusion pump system.

It is a more specific object of the present invention to provide an implantable manually-actuated micro-infusion pump system which provides increased protection against inadvertent actuation from externally applied pressures.

It is a further object of the present invention to provide a new and improved manually-actuated implantable micro-infusion pump system which provides a high degree of metering accuracy and is compact and economical to construct.

SUMMARY OF THE INVENTION

The present invention is directed to an implantable microinfusion pump system which includes a manually-actuated safety pump, a manually-actuated metering pump, and a fluid circuit serially interconnecting the pumps between a fluid reservoir and a dispensing site. Actuation of the safety pump allows a volume of fluid from the reservoir to enter the metering valve. Actuation of the metering pump causes a predetermined volume of the fluid advanced by the safety pump to be administered at the dispensing site.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
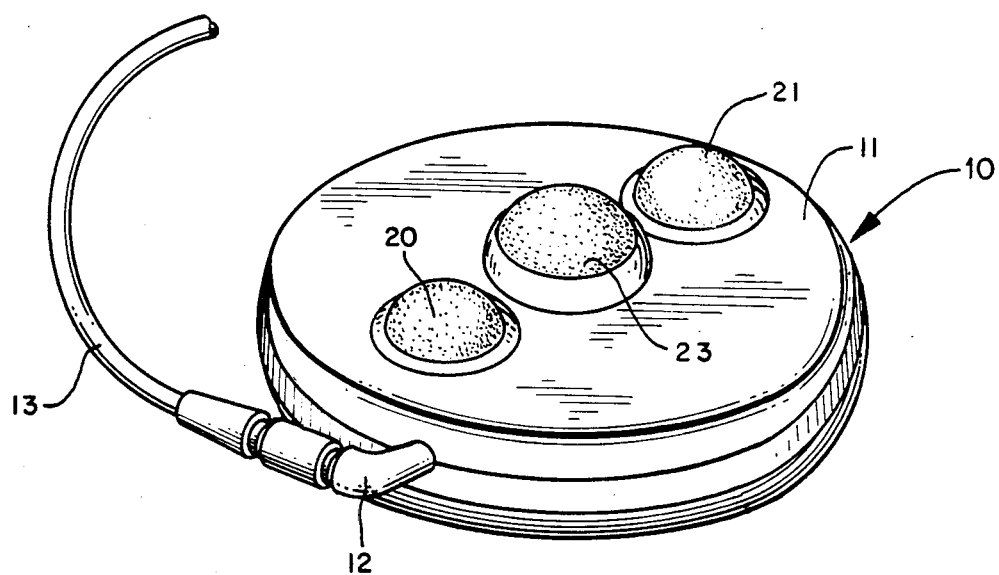
FIG. 1 is a perspective view of a combined pump and reservoir fluid dispensing system constructed in accordance with the invention.
Figure 2:
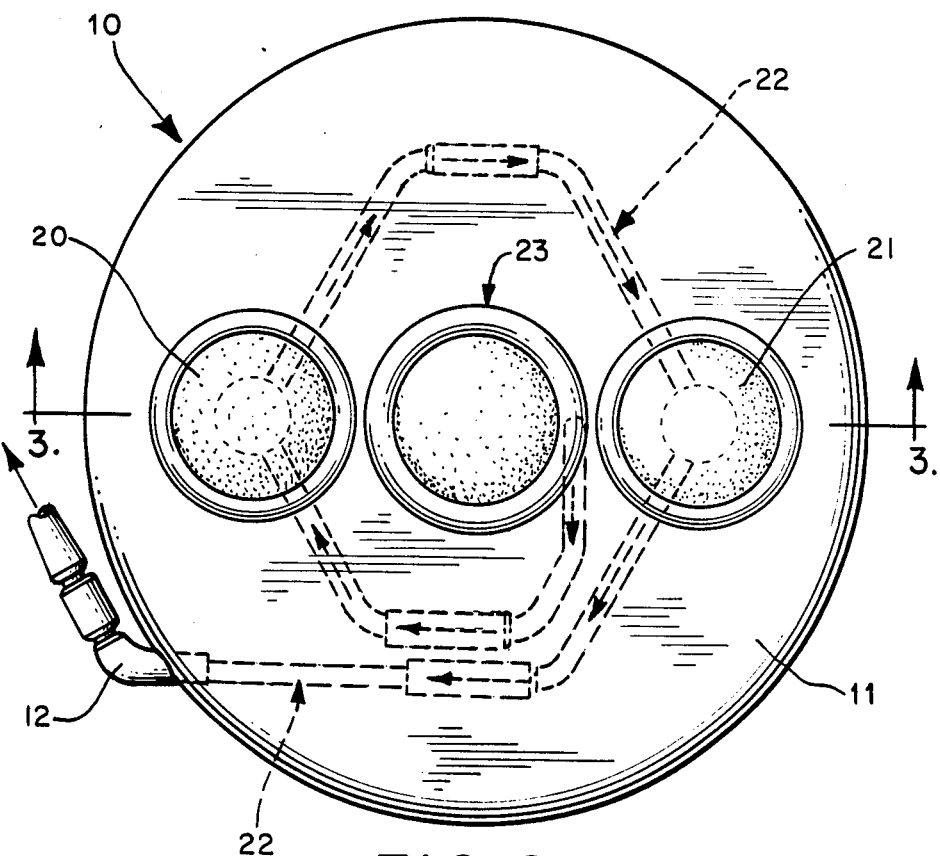
FIG. 2 is an enlarged top plan view of the dispensing system of FIG. 1 illustrating the fluid circuit contained therein.

Referring to the drawings, and particularly to FIGS. 1-4, a micro-infusion pump system constructed in accordance with the invention may be advantageously utilized in an implantable combined pump and reservoir medicament dispensing system 10. As seen in FIG. 1, this dispensing system includes a generally disc shaped housing 11 within which pump and reservoir elements are contained, and a dispensing port 12 from which medicament is dispensed to an administration site by means of a flexible catheter 13 of conventional construction. The dispensing system 10 is preferably of compact construction for implantation with minimal distress to the human body.

Figure 3:
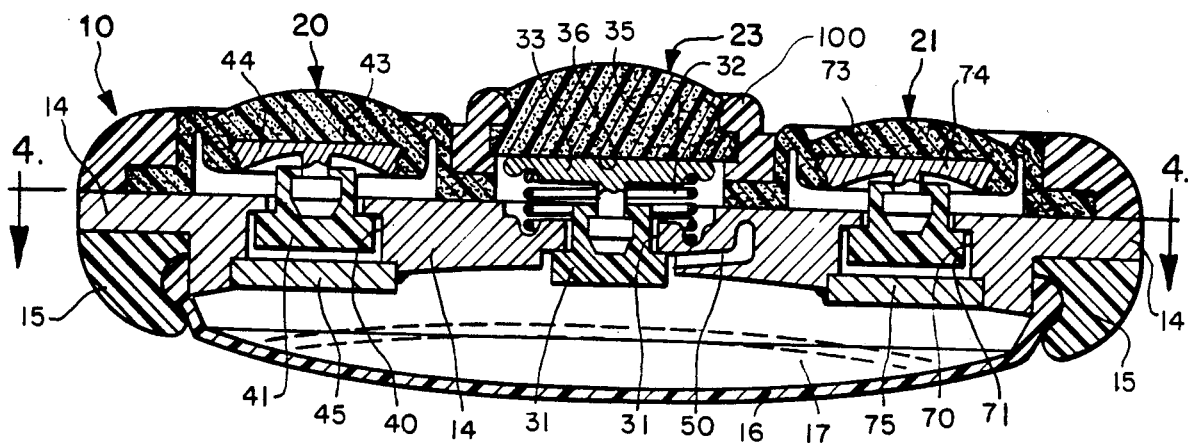
FIG. 3 is a cross-sectional view of the dispensing system taken along line 3—3 of FIG. 2.

Referring to FIG. 3, housing 11 is seen to include a base portion 14, which may be molded of a hard biocompatible material such as polyethersulfone and an overlying body portion 15 which may be molded of a biocompatible plastic such as polyethersulfone. The body portion defines a recess over which a flexible and expandable wall 16 of Dacron reinforced silastic material is provided to form an internal reservoir 17 within which a volume of medicament to be dispensed is stored.

To provide for the reliable dispensing of accurate dosages of medicament from reservoir 17, dispensing system 10 includes, in accordance with the invention, a safety pump 20 and a metering pump 21. These pump components, which are manually actuated by the application of pressure to the exterior surface of dispenser 10, are interconnected within housing 11 by means of a fluid circuit 22 such that upon actuation of safety pump 20 medicament (or other fluid in the reservoir of dispenser 10) passes from the reservoir to the metering pump 21. Then, upon actuation and release of the metering pump 21 the medicament is dispensed through dispensing port 12 to the delivery site.

In addition, the dispensing system 10 includes a fill port 23 through which medicament may be added to or removed from reservoir 17 as required. This fill port, which is described in the copending application of the present inventor entitled "Fill Port for an Implantable Fluid Reservoir", Ser. No. 484,571, filed concurrently herewith, is positioned generally in the center of housing 11 between the safety pump 20 and the metering pump 21. As developed in the copending application, this port allows convenient subcutaneous fluid communication with reservoir 17, while providing reliable protection against pressure-induced leakage from the reservoir.

Figure 4:
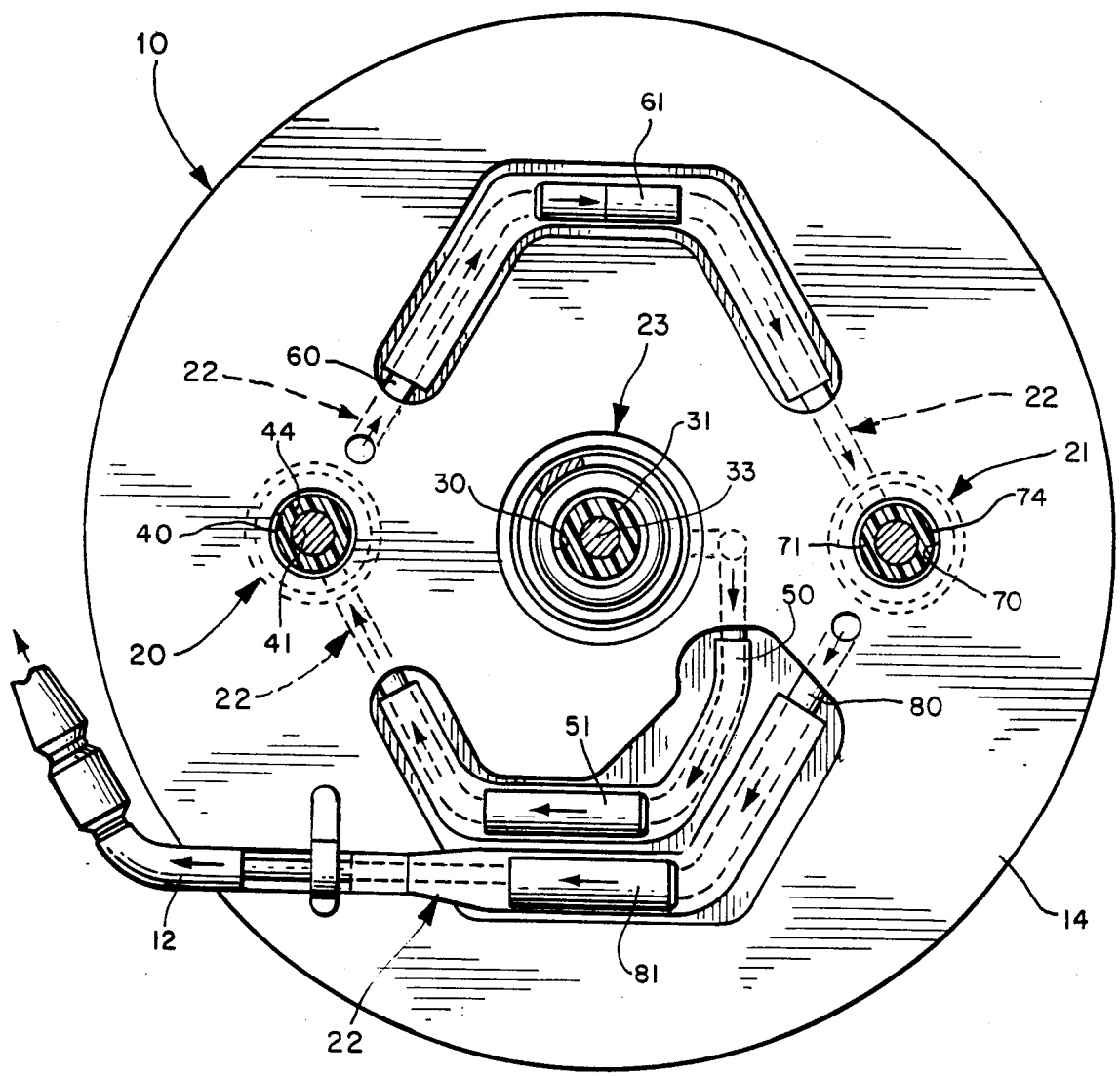
FIG. 4 is a cross-sectional view of the dispensing system taken along line 4—4 of FIG. 3 partially broken away to show the principal components of the fluid circuit contained therein.

Basically, as shown in FIGS. 3 and 4, fill port 23 is formed in part by an aperture 30 in base member 14 of housing 11. A valve member 31 extends through this aperture and includes an annular valving surface which engages a valve seat to control flow through the aperture. The valving member 31 is biased to a closed position by a helical spring 32 which bears against a valve actuator member 33 in mechanical engagement with the valving member. An overlying needle-penetrable fluid-impermeable cap member 35 formed of a bio-compatible rubber or silastic material is held in compressive engagement by the molded body portion 100 to provide a fluid-sealed chamber 36.

Upon insertion of a hypodermic needle (not shown) through cap member 35 valving member 31 is depressed, causing aperture 30 to open and permit the flow of fluid into and out of reservoir 17 through the needle. However, upon removal of the needle, valving member 31 is biased closed, aperture 30 is closed, and no fluid flow can take place. Of particular advantage is that increased pressure within reservoir 17, as may result from the application of external pressure to the flexible wall 16, results in valving member 31 being more firmly seated against its valve stop, thereby more positively closing aperture 30 to prevent undesired pressure flow from the reservoir.

Figure 5:
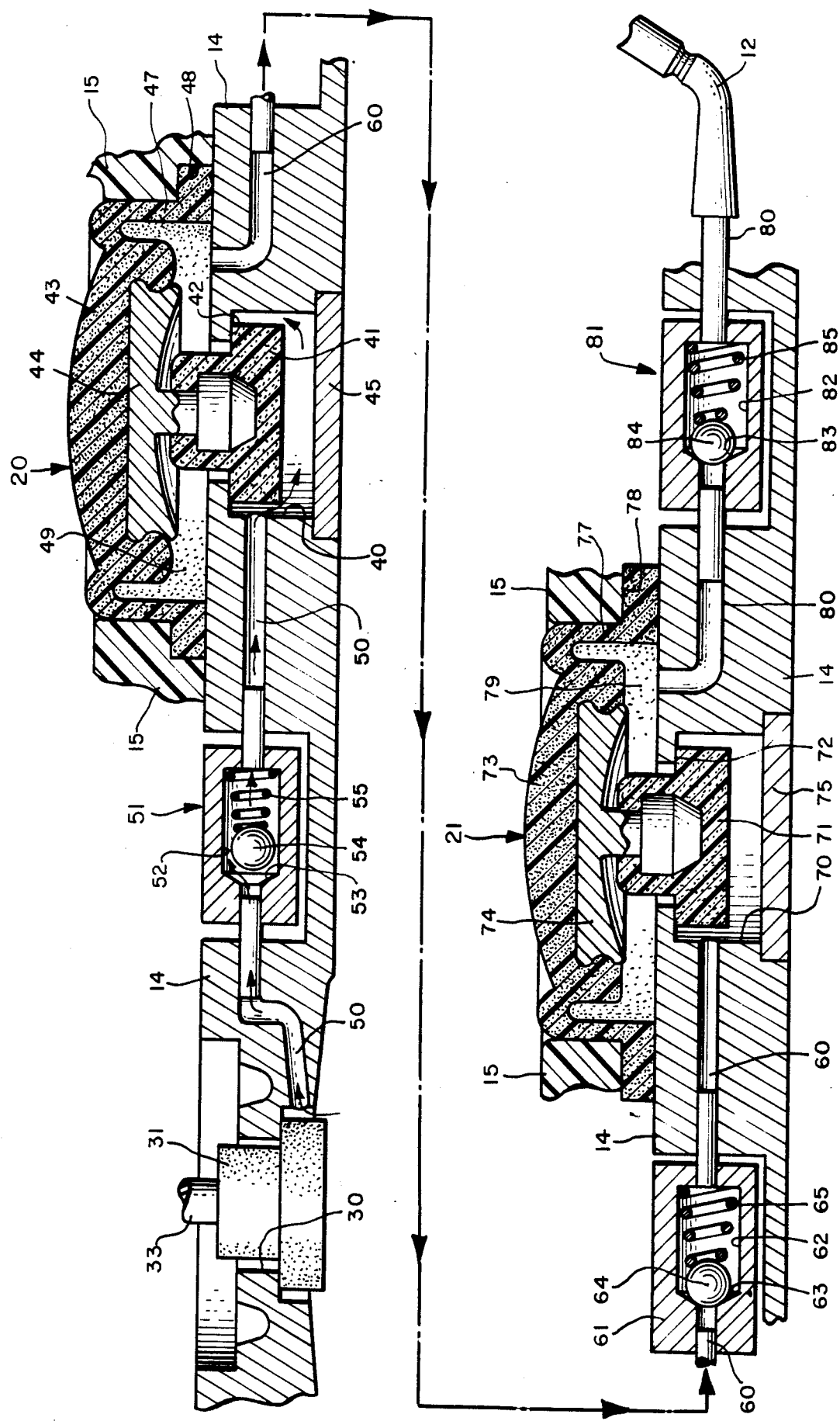
FIG. 5 is an enlarged cross-sectional view of the fluid circuit of the dispensing system showing the pump components thereof in a non-actuated state.

Referring to FIG. 5, safety pump 20 includes a pump chamber 40 formed in base portion 14, and a valving member 41 arranged for reciprocative movement within the aperture. In the non-actuated state of pump 20 valving member 41 is biased against an annular valve seat 42 provided on the sidewall of aperture 40 by means of a resilient cap member 43, which is mechanically coupled to valving member 41 by means of an actuator member 44. The bottom end of aperture 41 is closed by an end plate. Cap member 43 includes an annular downwardly projecting rim portion 47 which engages an appropriately dimensioned channel 48 in the body portion 15 of housing 11 such that a second fluid-sealed pump chamber 49 is formed between cap member 43 and base member 14.

In the non-actuated porition of the safety pump 20 shown in FIG. 5 liquid medicament in reservoir 17 enters the safety pump chamber 40 through a first conduit segment 50 which includes an in-line check valve component 51. This component, which may be conventional in construction and operation, includes a valve chamber 52 having a tapered valve seat 53 at one end against which a spherical valving element 54 is caused to bear by a spring member 55. The effect of check valve 51 is to allow flow from reservoir 17 into chamber 46, but to prevent flow in the reverse direction from chamber 46 to reservoir 17.

Safety pump 20 is actuated by application of a force on cap member 43. This displaced valving member 41 from valve seat 42, opening aperture 40 to fluid flow. At the same time, the downward movement of valving member 41, cap member 43, and actuator member 44 causes medicament in chambers 40 and 49 to flow through a conduit segment 60 to metering pump 21. To prevent reverse flow an in-line check valve component 61 is included in segment 60. This check valve, which may be conventional in construction and operation, includes a valve chamber 62 having a tapered valve seat 63 at one end against which a spherical valve member 64 is biased by a spring 65. The effect of check valve assembly 61 is to allow fluid flow from safety pump 20 to metering pump 21, but to preclude fluid flow in the reverse direction from metering pump 21 to safety pump 20.

The metering pump 21 is seen to comprise a pump chamber 70 formed in base member 14, and a valving member 71 arranged for reciprocative movement within the chamber. The valving member 71 is biased against an annular valve seat 72 by a resilient cap member 73, which is mechanically coupled to the valving member 70 by an actuator member 74.

Cap member 73 includes an annular flange portion 77 which engages an annular channel 78 in base member 24 to provide a fluid-sealed engagement and upward bias on valving member 71. As a consequence of the sealed engagement, a second pump chamber 79 is formed above base member 24.

In the non-actuated state of metering pump 21 valving member 71 is biased against valve seat 72, and chamber 70 is sealed from chamber 79. Consequently, fluid advanced along conduit segment 60 by safety pump 20 enters only chamber 70 through check valve 61.

Upon actuation of metering pump 21 valving member 71 is displaced downwardly into pump chamber 70, causing medicament in the chamber to enter chamber 79 and advance along a conduit segment 80 toward dispensing port 12. To preclude reverse flow through conduit segment 80, the conduit segment includes an in-line check valve component 81. This check valve, which may be conventional in construction and operation, includes a valve chamber 82 having a tapered valve seat 83 at one end. A spherical valve member 84 is biased against the valve seat by a spring 85 within the valve chamber. In operation, check valve 81 opens to permit flow from metering pump 21 to dispensing port 12, but closed to preclude flow in the reverse direction from dispensing port 12 to the metering port.

As shown in FIG. 5, with pumps 20 and 21 in their non-actuated states, medicament from reservoir 17 is drawn through check valve 51 to chamber 40 of safety pump 20. This is accomplished upon return of valving member 41 to its non-actuated position, the biasing force exerted by cap member 43 exceeding the biasing force of spring 55 of check valve 51. Since metering valve 21 is closed at this time, no flow takes place in conduit segments 60 and 80.

Figure 6A:
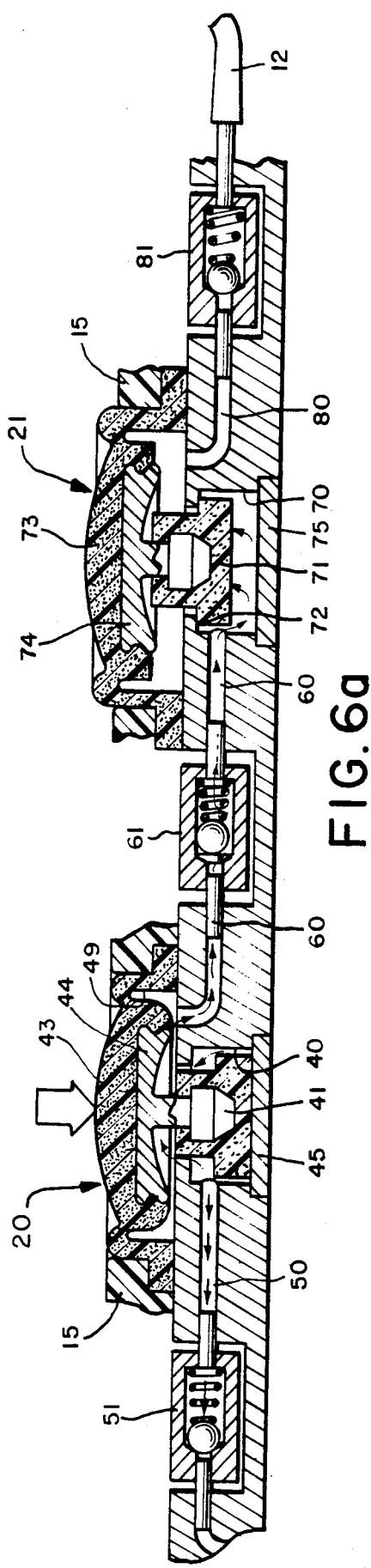
FIG. 6a is a cross-sectional view of a portion of the fluid circuit illustrating fluid flow therein upon actuation of the safety pump component of the circuit.

Referring to FIG. 6a, to dispense medicament it is necessary for the user to first push and release safety pump 21. As shown in FIG. 6a, the movement of plunger 41 into chamber 40 and the movement of actuator member 14 into chamber 49 causes medicament from these chambers to be forced through conduit segment 60 and check valve 61 into chamber 70 of metering pump 21. Since plunger 71 is forced against valve stop 72, no flow is possible through metering pump 21.

In accordance with the invention, the restoring force of cap member 73 on plunger 71 is of itself insufficient to open check valve 61, so that medicament can be drawn into pump chamber 70 only upon the application of external force to cap member 43 of safety pump 20. After safety pump 20 has been depressed and released, check valve 61 closes and cap member restores plunger 41 to its closed position. This causes medicament to be drawn from reservoir 17 through conduit segment 50 to refill valve chamber 40.

Figure 6B:
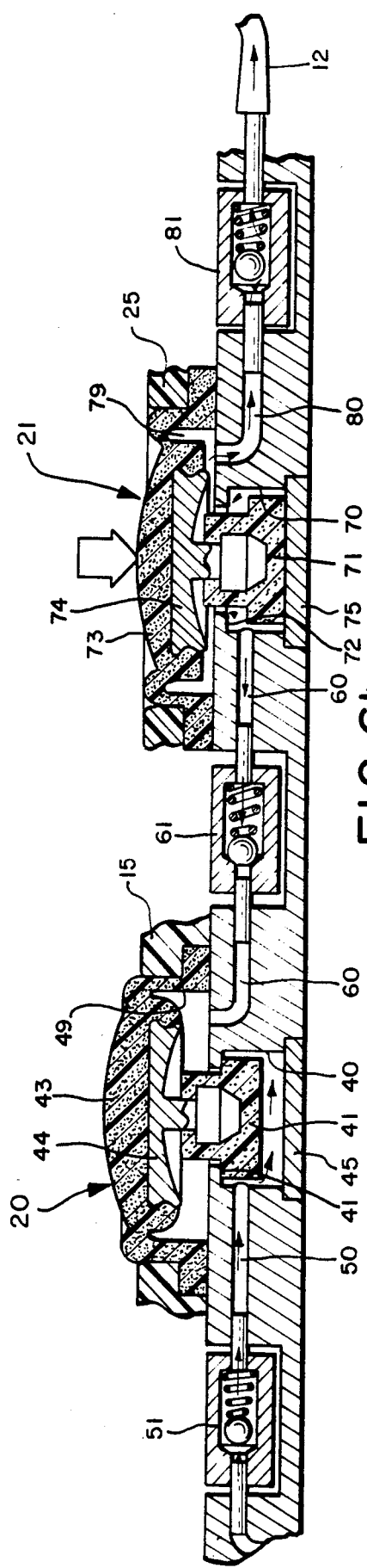
FIG. 6b is a cross-sectional view similar to FIG. 6a illustrating fluid flow in the fluid circuit upon actuation of the metering pump component of the circuit.

Next, as shown in FIG. 6b, metering pump 21 is actuated. As plunger 71 enters chamber 70 and actuator member 74 enters chamber 79 medicament is displaced from chambers 70 and 79 through conduit segment 80 and check valve 81 to dispensing port 12. At the same time, check valve 61 is forced closed, preventing medicament flow from metering pump 21 to safety pump 20. Since the same volume of medicament is always displaced by plunger 71 and actuator member 74, the volume of medicament dispensed through conduit segment 80 with each actuation of metering pump 21 is constant.

By reason of the serial arrangement of the safety and metering pumps, it is necessary that the metering pump 20 be first depressed and released before the metering pump 21 will be operative to dispense a dosage of medicament. This precludes inadvertent actuation of the dispensing system, since the operator must consciously alternately actuate the safety and metering pumps or actuator buttons for each intended dose. A single applied force, as exerted by pressure on the body, will not cause the dispensing system to function.

Furthermore, the application of pressure on the medicament in reservoir 17 merely serves to bias the safety valve 20 more tightly closed. Moreover, even in the event of failure of the safety pump, pressure in reservoir 17 would only serve to bias the metering pump 21 closed. Thus, a double safety is provided against uncontrolled pressure flow.

While the metering system of the invention has been shown in conjunction with a combined pump and reservoir dispensing system, it will be appreciated that the metering system can be utilized apart from the reservoir, as where the reservoir is connected to the safety pump 20 by a flexible catheter or other appropriate means. In this instance, the reservoir and pumping system could be provided in separate implantable housings connected by this conduit.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:
1. A dispensing system for dispensing a metered volume of fluid from a reservoir to a dispensing port, comprising:
   a housing;
   a reservoir;
   means within said housing defining a fluid circuit serially including a first check valve, a safety pump, a second check valve, a metering pump, and a third check valve;
   said safety pump being operable in response to the application of a first force applied externally to said housing for advancing fluid through said second check valve to said metering pump; and
   said metering pump being operable in response to the application of a second force applied externally to said housing for advancing a predetermined volume of said fluid advanced from said safety pump through said third check valve to said dispensing port.

2. A dispensing system as defined in claim 1 wherein said metering pump includes bias means for restoring said pump to a fluid receiving condition, and wherein said biasing means exert a force on fluid in said metering pump less than that exerted thereon by said second check valve.

3. A dispensing system as defined in claim 1 wherein said first check valve closes at a lower pressure than said second and third check valves, said safety pump includes bias means for restoring said pump to a fluid receiving condition and said restoring force exceeds the closing force of said first check valve.

4. A dispensing system as defined in claim 1 wherein the reservoir is at least partially defined by said housing and includes a flexible and expandable fluid impermeable membrane.

5. A dispensing system as defined in claim 1 wherein said metering pump comprises a plunger-type pump including an actuator actuable from the exterior of said housing.

6. A dispensing system as defined in claim 5 wherein said safety pump comprises a plunger-type pump including an actuator stem actuable from the exterior of said housing.

7. An implantable manually-actuated dispensing system for dispensing a metered volume of fluid from a reservoir through a dispensing port, comprising:
   an implantable housing defining a fluid circuit extending between the fluid reservoir and the dispensing port;
   safety pump means within said housing operable in response to a first applied force;
   metering pump means within said housing operable in response to a second applied force;
   said fluid circuit serially including said safety pump means and said metering pump means;
   said safety pump means being operable in response to the application of said first applied force for advancing said fluid along said fluid circuit to said metering pump, and preventing the flow of fluid from the fluid reservoir to said metering pump in the absence of said application of said applied force; and
   said metering pump means being operable in response to the application of a second applied force for advancing a predetermined volume of said fluid advanced from said first pump along said fluid circuit to the dispensing port.

8. A dispensing system as defined in claim 7 wherein said housing further defines the fluid reservoir.

9. A dispensing system as defined in claim 8 wherein said fluid circuit includes a check valve between said reservoir and said safety pump means.

10. A dispensing system as defined in claim 7 wherein said fluid circuit includes a check valve between said safety pump means and said metering pump means.

11. A dispensing system as defined in claim 10 wherein said fluid circuit includes an additional check valve between the reservoir and said safety pump means.

12. A dispensing system as defined in claim 7 wherein said safety valve means are biased closed by fluid pressure in the fluid reservoir.

13. An implantable dispensing system for dispensing a predetermined dosage of fluid from a reservoir to a dispensing site, comprising:
- a housing defining first and second pump chambers and a fluid circuit serially interconnecting the reservoir, said chambers and the dispensing site;
- safety pump means including a first plunger disposed in said first pump chamber, said plunger being actuable by application of a first externally applied force to advance a predetermined volume of fluid from said first pump chamber through said fluid circuit to said second chamber; and
- metering pump means including a plunger disposed in said second pump chamber, said plunger being responsive to application of a second externally applied force for urging a predetermined dosage of fluid from said volume advanced by said safety pump means from said second chamber through said fluid circuit to the dispensing site.

14. An implantable dispensing system as defined in claim 13 wherein said fluid circuit includes a check valve between said safety pump and said metering pump.

15. A dispensing system as defined in claim 14 wherein said metering pump means include biasing means for restoring said plunger to fluid receiving position and said biasing means exert a force on said fluid less than that exerted thereon by said check valve.

16. A dispensing system as defined in claim 14 wherein said fluid circuit includes an additional check valve between the reservoir and said first pump chamber.

17. An implantable dispensing system as defined in claim 13 further including:
- a dispensing port;
- a first passageway between the reservoir and said first pump chamber, said passageway including a first check valve;
- a second passageway between said first pump chamber and said second pump chamber, said second passageway including a second check valve; and
- a third passageway between said second pump chamber and said dispensing port.

* * * * *

UNITED STATES PATENT AND TRADEMARK OFFICE
CERTIFICATE OF CORRECTION

PATENT NO. : 4,548,607
DATED : October 22, 1985
INVENTOR(S) : Donald L. Harris

It is certified that error appears in the above-identified patent and that said Letters Patent are hereby corrected as shown below:

Col. 1, line 36: Change "0.1" to --0.5--.
line 38: Change "0.6" to --3--.

Signed and Sealed this

Twenty-second Day of December, 1987

Attest:

DONALD J. QUIGG

*Attesting Officer*         *Commissioner of Patents and Trademarks*